United States Patent [19]

Schaerfl, Jr. et al.

[11] Patent Number: 5,302,755
[45] Date of Patent: Apr. 12, 1994

[54] METHOD FOR DMTDA PRODUCTION

[75] Inventors: Robert A. Schaerfl, Jr.; Gordon G. Knapp; W. Dirk Klobucar, all of Baton Rouge, La.

[73] Assignee: Ethyl Corporation, Richmond, Va.

[21] Appl. No.: 968,248

[22] Filed: Oct. 29, 1992

Related U.S. Application Data

[63] Continuation of Ser. No. 708,470, May 31, 1991, abandoned.

[51] Int. Cl.$^5$ ............................................ C07C 319/14
[52] U.S. Cl. .................................................. 564/440
[58] Field of Search .................. 564/440; 568/57; 502/33, 244, 225; 423/471

[56] References Cited

U.S. PATENT DOCUMENTS

| | | | |
|---|---|---|---|
| 4,594,453 | 6/1986 | Ranken et al. | 564/440 |
| 4,670,597 | 6/1987 | Ranken et al. | 564/440 |
| 4,670,598 | 6/1987 | Davis | 564/440 |
| 4,731,446 | 3/1988 | Pearson et al. | 544/281 |
| 4,751,330 | 6/1988 | Davis | 564/440 |
| 4,825,002 | 4/1989 | Davis | 564/438 |
| 4,889,955 | 12/1989 | Ranken | 564/440 |

FOREIGN PATENT DOCUMENTS 1072605 6/1967 United Kingdom .

OTHER PUBLICATIONS

CA113(19):171655y, Hargis (1990).
CA112(19):178309b, Dixon et al. (1989).
CA111(15):133696p, Palkovics et al (1988).
CA111(4):25319j, Mueller (1989).
CA111(1):6983e, Ranken et al (1989).
CA110(12):97558p, Pierantozzi (1988).
CA110(9):75028p, Palkovics et al. (1988).
CA110(3):23514z, Takahata et al. (1988).
CA110(1):7741r, Wu et al (1988).
CA109(21):189983f Pasek et al, (1986).
CA108(21):186309j Hargis, (1988).
CA108(20):169623q Pierantozzi (1987).
CA108(12):96625e Agrawal et al. (1987).
CA108(5):37367z Dixon et al (1987).
CA107(8):61023j Ranken et al (1987).
CA107(5):39359b Okuno et al (1986).
CA106(19):156039n Takahata et al. (1986).
CA106(17):138075s Takahata et al. (1986).
CA106(17):138074r Takahata et al (1986).
CA106(7):49761v Hargis (1986).
CA106(6):35077q Hargis (1986).
CA103(25):214961h Hargis (1985).
CA101(1):6977z Davidson et al. (1984).
CA97(23):197972a Takahata et al (1982).
CA94(19):156513w, Schulte-Huermann et al, (1980).
CA94(15):121069d, Malz et al. (1980).
CA94(3):15377t, Brandt et al., (1980).
CA92(13):110651v, Volf et al, (1979).
CA92(3):22227f, Schneider, (1979).
CA90(21):168251q, Dobrovol'skii et al. (1979).
CA90(3):22552s Motoyama et al. (1978).
CA89(15):129234w Schneider (1978).
CA88(26):192408a Kirpichev et al (1978).
CA88(25):190363h Nakagawa et al. (1977).
CA87(17):134466m Hargis (1977).
CA84(9):58884s Klopfer (1975).
CA82(19):125054v Dunn (1975).
CA77(15):101113j Klopfer (1972).
CA76(23):140158b Napolitano (1972).
CA75(19):118106r Grimm (1971).
CA73(7):35021s Klopfer (1970).
CA73(3):14431k Greenfield et al. (1970).
CA69(3):10188f Richards et al. (1968).
CA68(21):95486d Dovell et al. (1967).
CA93(9):94514r Hronec et al. (1980).

*Primary Examiner*—Allen J. Robinson
*Assistant Examiner*—P. O'Sullivan
*Attorney, Agent, or Firm*—Richard J. Hammond

[57] ABSTRACT

Thioalkylated aromatic amines are prepared by reacting a mixture of an aromatic amine, an organic disulfide and a Lewis acid or organometallic catalyst to form a product mixture and adding to said product mixture a poly(oxyalkylene)polymer or by reacting a mixture of an aromatic amine, an organic disulfide and a Lewis acid or organometallic catalyst in the presence of a poly(oxyalkylene)polymer for the purpose of easy handling of the catalyst residue for recycling.

12 Claims, No Drawings

METHOD FOR DMTDA PRODUCTION

This is a continuation of copending application Ser. No. 07/708,470 filed on May 31, 1991, now abandoned.

This invention relates, broadly, to an improved process for the production of alkylated or thioalkylated aromatic diamines. More specifically, this invention relates to an improved process for the production of dimethylthiotoluenediamine (DMTDA).

BACKGROUND OF THE INVENTION

As disclosed in U.S. Pat. No. 4,594,453 (Ranken et al.), it is known that various (hydrocarbylthio) aromatic amines are useful as intermediates in the preparation of biologically active materials, polyurethanes, etc., and they can be prepared by reacting an aromatic amine with a hydrocarbyl disulfide in the presence of a Lewis acid catalyst. The preferred catalysts of Ranken et al. are metal halides, such as aluminum chloride, boron trifluoride, boron trichloride, ferric chloride and zinc chloride.

U.S. Pat. No. 4,670,597 (Ranken et al.) discloses the preparation of (hydrocarbylthio) aromatic amines by the hydrocarbylthiolation of aromatic monoamines with a hydrocarbyl disulfide in the presence of Lewis acid catalysts selected from hydrogen iodide, ammonium iodide, and copper iodide.

U.S. Pat. No. 4,751,330 (Davis) discloses the preparation of (hydrocarbylthio) aromatic amines by the hydrocarbylthiolation of aromatic amines in the presence of metal or metal halide catalysts, with particularly good results noted with the use of copper, zinc, or ferric, ferrous, or aluminum chloride.

U.S. Pat. No. 4,825,002 (Davis) discloses removal of a Lewis acid contaminant from a (hydrocarbylthio)aromatic amine by mixing a solid alkali metal hydroxide with a solution of the Lewis acid in the (hydrocarbylthio)aromatic amine, preferably at about 110°–120° C., and then filtering said solids from the mixture.

OBJECTS OF THE INVENTION

In the present preparation of DMTDA, toluenediamine is reacted with dimethyldisulfide in the presence of copper iodide to form monomethylthiotoluenediamine (MMTDA) and DMTDA, successively. Under the present procedures for preparing DMTDA, the catalyst must be replaced for a subsequent thioalkylation reaction. This is due to a loss of catalytic ability resulting from the temperature conditions of the product recovery portion of the thioalkylation process.

Accordingly, an object of this invention is to provide an improved process for the production of thioalkylated aromatic diamines.

Another object of this invention is to increase the yields of dimethylthiotoluenediamine which may be formed in the presence of a given amount of Lewis acid catalyst or organometallic catalyst.

Still further, an object of this invention is to provide a process for the formation of dialkylthiotoluenediamines in which the catalyst may be recycled.

DESCRIPTION OF THE PREFERRED EMBODIMENTS

In accordance with the present invention, an aromatic amine is reacted with an organic disulfide in the presence of a catalyst resulting in the formation of hydrocarbylthio aromatic amines.

Aromatic amines utilizable in the practice of the above-mentioned hydrocarbylthiolation process include compounds having at least one amino group attached to a carbocyclic or heterocyclic ring of an aromatic compound containing one or more simple and/or fused rings, such as benzene, naphthalene, anthracene, pyrrole, pyridine, indole, etc. The process may also utilize reactive heterocyclic amines, such as pyrrole, indole, imidazole, etc. The compounds may bear no substituents other than the required amino group(s) or they may bear substituents which are inert to the reaction conditions, such as one or more additional amino groups or substituents such as chloro, fluoro, alkyl, aryl, alkaryl or aralkyl groups on any positions other than those substituted by hydrocarbylthio groups. Examples of useful compounds include 4-(phenylthio)aniline, 2-aminobiphenyl, 4-phenoxyaniline, aminobenzenes containing one or two amino groups, such as aniline, 4-butylaniline, 4-methylaniline, 4-chloroaniline, 2-ethylaniline, N-methylaniline, 2,4- and 2,6-diaminotoluenes, 2,6-diamino-1-ethylbenzene, etc.

Organic disulfides which may be reacted with the aromatic amines include saturated and unsaturated aliphatic, cycloaliphatic and aromatic disulfides in which the hydrocarbyl groups optionally bear inert substituents, such as chloro substituents. Examples of such substituents are methyl, ethyl, propyl, n-butyl, sec-butyl, tert-butyl, 2-chlorophenyl, cyclopentyl, cyclohexyl, phenyl, benzyl, p-tolyl and p-chlorophenyl disulfides, etc. The hydrocarbyl disulfide component of the reaction mixture is generally included in at least the stoichiometric amount required to produce the desired hydrocarbylthio aromatic amine. For example, at least one equimolar amount is used when a mono(hydrocarbylthio)aromatic amine is desired and at least two equimolar amounts are used when a di(hydrocarbylthio)aromatic amine is desired.

The reaction of the aromatic amine with the hydrocarbyl disulfide is generally conducted at a temperature in the range of about 20° C. to 300° C. and at a pressure of atmospheric up to about 1000 psi in the presence of a catalyst. Suitable catalysts are Lewis acid catalysts, such as metal halides. Examples of such Lewis acid catalysts are copper chloride, copper bromide, copper iodide, ammonium iodides, hydrogen iodide, zinc iodide, ferrous iodide, cobaltous iodide, aluminum chloride, boron trifluoride, ferric chloride, zinc chloride, zinc iodide, etc. Metal alkyls, such as triethylaluminum, diethylaluminum chloride, ethyl aluminum dichloride, etc., and the organometallic compounds derived from the reaction of the aromatic amine with the metal alkyls and reactive metals such as aluminum may also be utilized.

In conducting the (hydrocarbylthio)alkylation process, it is generally preferred to (1) heat a mixture of the catalyst and aromatic amine at a suitable temperature, e.g., about 100° C. to about 200° C.; and then (2) continue to heat the reaction mixture at reflux temperature after the disulfide has been added to effect a hydrocarbylthiolation process while removing evolved hydrocarbyl thiol by-product from the reaction vessel. However, it is also satisfactory to conduct the process by simply mixing the catalyst and reactants together and heating them to reflux temperature. An inert solvent may be employed if desired, but is unnecessary.

It is desirable to provide a process by which the catalyst utilized by the present process may be collected and reused in subsequent (second) reaction mixtures. As mentioned above, physical separation methods, such as catalyst precipitation/centrifugation methods, are possible means of collecting the catalyst, but prove impractical as recycling methods because of the rock-like nature of catalyst which remains after removing product when no chaser is used. Further, treatment of the catalyst with certain bases renders the catalyst ineffective for subsequent thioalkylation processes. Therefore, it is equally prudent to utilize a means which allows practical and effective re-use of the catalyst.

Such re-use would involve introducing the recycled catalyst into a second, subsequent reaction mixture comprising an aromatic amine and an organic disulfide to produce a mixture including the desired thioalkylated aromatic amines. A second reaction mixture may also contain additional components which do not inhibit the subsequent (second) thioalkylation reaction. Examples of such additional components would include additional solvent(s), catalyst(s), inert gases, etc.

In accordance with the present invention, a poly(oxyalkylene)polymer is added to the reaction mixture to serve as a chaser to the Lewis acid or organometallic catalyst. For the purposes of this application, a poly(oxyalkylene)polymer shall mean oxygen-containing alkylene polymers. To be suitable for this method, the poly(oxyalkylene)polymer must be soluble in organic solvents. In addition, the poly(oxyalkylene)polymer should have a boiling point such that it will not be removed from the reaction mixture prior to the recovery of the desired product. Various poly(oxyalkylene)-polymers may be utilized as the base in this process.

Examples of useful oxygen-containing alkylene polymers include alkylene diols such as 1,2-octanediol, 1,2-decanediol, 1,3-decanediol and alkylene ether glycols such as polyethylene glycol $H(OCH_2C_2H)_nOH$, polypropylene glycol, polybutylene glycol and poly(1,3-butylene)glycol. Also useful are alkyl- or aryl-terminated alkylene ether polymers, wherein the aryl terminating group is substituted or unsubstituted, such as those seen in the Brij® polyoxyethylene series (ICI Corp.), the Lipopeg® series (Lipo Chemicals), the Atlas® 6 series (ICI Corp.), and the Igepal® CO series (GAF Corp.).

The examples that follow exemplify the present invention, but are not intended to limit the scope of the invention.

EXAMPLES

In the following product recovery tests (Examples 1 and 2), a continuous flash unit was utilized. In each of these tests, product recovery will be indicated by percentage of DMTDA in the flash distillate.

EXAMPLE 1

Baseline Thioalkylation Run

In a 100 mL round bottom three-neck flask, equipped with a magnetic stirrer, condenser, heating mantle, nitrogen flush and dropping funnel, was added 20.0 g of Aldrich 2,4-toluenediamine (TDA) and 3.0 g of $Cu_2I_2$. The flask contents were flushed with nitrogen and heated to approximately 145° C. Dimethyldisulfide (DMDS) was then added slowly over a six-hour period to maintain a temperature of 140°-60° C. Samples were taken occasionally for GC analysis, as shown in the following table:

TABLE I

| SAMPLE # | TIME (Hr) | DMDS (ml) | TDA (Area %) | MMTDA (Area %) | DM-c-TDA (Area %) |
|---|---|---|---|---|---|
| 0 | 0.0 | 0 | * | * | * |
| 1 | 1.0 | 15 | 34.8 | 49.2 | 16.5 |
| 2 | 2.0 | 22 | 11.8 | 48.2 | 40.0 |
| 3 | 3.0 | 28 | 4.8 | 37.3 | 57.8 |
| 4 | 4.5 | 33 | 0 | 12.6 | 85.9 |
| 5 | 5.0 | 33 | 0 | 11.2 | 87.6 |
| 6 | 6.0 | 38 | 0 | 2.26 | 95.6 |

*Start adding DMDS.

The reaction mixture was cooled and 8.8 g of PEG 600 was added and then the mixture was distilled in a Kugelrohr apparatus. The product (distillate, 26.2 g; 75% yield) was removed at up to 179° C.0.6 torr. The catalyst residue (PEG 600, $Cu_2I_2$) was left in the flask which was reused in the following run.

First Thioalkylation Using Recycled Catalyst

In the same 100 mL round bottom three-neok flask containing the above-mentioned catalyst residue, 20.0 g of 2,4-toluenediamine was added. The mixture was blanketed with nitrogen and then the mixture was heated to 150° C. and 50 mL of DMDS was added (keeping the temperature > 140° C.) over a period of 3 hours. The reaction mixture was held at 140°-160° C. for a total of 7 hours. Samples were taken occasionally, with the final sample indicating an area % of 3.1% MMTDA and 96.5% DMTDA. The reaction mixture was stripped in a Kugelrohr apparatus first at 88° C./0.28 torr to remove unreacted DMDS and then at 181° C./0.42 torr for a half hour to remove the DMTDA (36.6 g; 87% yield) and a residue of 11.7 g.

Second Thioalkylation Using Recycled Catalyst

The same 100 mL flask containing the catalyst residue of the first thioalkylation using the recycled catalyst was used to conduct a third thioalkylation (a second "recycled" use of the catalyst residue). To the above-mentioned flask 20.0 g 2,4-toluenediamine was added. The mixture was blanketed with nitrogen and then heated to 150° C. and 41 mL dimethyldisulfide was added, keeping the temperature > 140° C. This reaction mixture was sampled occasionally, with the final sample (at 6 hours) indicating 7.5 area % MMTDA and 91.5 area % DMTDA.

EXAMPLE 2

Using Less Catalyst With Recycle

In a 100 mL round bottom three-neck flask, equipped with a magnetic stirrer, heating mantle, condenser, nitrogen flush, and dropping funnel, was added 20.0 g of Aldrich 2,4-toluenediamine and 1.0 g of $Cu_2I_2$. The flask contents were flushed with nitrogen and heated to approximately 145° C. DMDS was added slowly over an eight-hour period to maintain a temperature of 140°-160° C. Samples were taken occasionally for GC analysis as indicated in the following table.

TABLE II

| SAMPLE # | TIME (Hr) | DMDS (ml) | TDA (Area %) | MMTDA (Area %) | DMTDA (Area %) |
|---|---|---|---|---|---|
| 0 | 0.0 | 0 | * | * | * |
| 1 | 1.0 | 10 | 44.8 | 52.0 | 3.3 |
| 2 | 2.0 | 17 | 23.6 | 52.9 | 23.4 |
| 3 | 4.0 | 22 | 11.5 | 50.5 | 37.8 |
| 4 | 5.5 | 25 | 7.0 | 46.4 | 47.0 |

TABLE II-continued

| SAMPLE # | TIME (Hr) | DMDS (ml) | TDA (Area %) | MMTDA (Area %) | DMTDA (Area %) |
|---|---|---|---|---|---|
| 5 | 6.0 | 34 | 3.4 | 33.1 | 63.5 |
| 6 | 7.0 | 34 | 0 | 15.6 | 83.9 |
| 7 | 7.8 | 42 | 0 | 9.2 | 90.1 |
| 8 | 9.0 | 42 | 0 | 6.5 | 92.7 |

*Start adding DMDS.

10.0 g PEG 600 was added and then the reaction mixture was distilled in a Kugelrohr apparatus. The product was removed at up to 189° C./0.38 torr and weighted 26.18 g (75% yield). The catalyst residue (11.0 g) was left in the flask and used in the next run.

Thioalkylation Using Recycled Catalyst

In the same 100 mL round bottom three-neck flask (above) containing the 11.0 g catalyst residue, 20.0 g 2,4-toluenediamine was added. The mixture was blanketed with nitrogen and then the mixture was heated to about 150° C. and 28 dimethyldisulfide was added over time to maintain a reaction temperature >140° C. Samples were taken occasionally over the course of the reaction, with the final sample (at 10.25 hours) indicating 4.0 area % MMTDA and 96.0 area % DMTDA.

The reaction mixture was stripped in the Kugelrohr apparatus first at 100° C./0.28 torr to remove unreacted DMDS and then at 190° C./0.3 torr for a half hour to remove the product (28.4 g; 81% yield) and leaving a catalyst residue of 9.37 g.

Second Recycle

In the same 100 mL flask containing 9.37 g catalyst residue (above) was added 20.0 g 2,4-toluenediamine. The mixture was blanketed with nitrogen and then heated to about 150° C. and DMDS was added over time to maintain a reaction temperature >140° C. Samples were taken occasionally over an eight-hour period, with the final sample indicating 7.0 area % MMTDA and 92.9 area % DMTDA.

The DMDS was stripped in the Kugelrohr apparatus at 94° C./2.0 torr followed by 27.7 g (79% yield) of the product at 184° C./0.34 torr, leaving a catalyst residue of 7.7 g.

What is claimed is:

1. In a process for producing thioalkylated toluene diamines comprising allowing a reaction mixture comprising
   a) a toluenediamine having no substituents other than the required amino groups or having one or more substituents which are inert to the reaction conditions,
   b) an organic disulfide, and
   c) A Lewis acid or organometallic catalyst to form a product mixture and removing the desired thioalkylated toluene diamines from said product mixture by a thermal product recovery method, the improvement comprising adding to said reaction mixture a chaser selected from the group consisting of alkylene diol, alkylene ether glycol, alkyl-terminated alkylene ether polymer and aryl-terminated alkylene ether polymer said chaser having the following properties: a) it is soluble in the organic compounds of the reaction mixture and b) it has a boiling point such that it will not be removed from the product mixture prior to the recovery of the desired product.

2. In a process for producing thioalkylated toluene diamines from a first reaction mixture comprising a) a toluene diamine having no substituents other than the required amino groups or having one or more substituents which are inert to the reaction conditions, b) a Lewis acid or organometallic catalyst, c) an organic disulfide and d) a chaser selected from the group alkylene diol, alkylene ether glycol, alkyl-terminated alkylene ether polymer and aryl-terminated alkylene ether polymer said chase having the following properties: a) it is soluble in the organic compounds of the reaction mixture and b) it has a boiling point such that it will not be removed from the product mixture prior to the recovery of the desired product, said first reaction mixture forming a product mixture from which the desired thioalkylated toluene diamines are removed by thermal product recovery methods, the improvement comprising recycling the chaser and Lewis acid or organometallic catalyst by:
   i) separating the chaser and Lewis acid or organometallic catalyst from the product mixture, and
   ii) treating a second reaction mixture with the separated chaser and Lewis acid or organometallic catalyst.

3. In a process for producing thioalkylated toluene diamines from a first reaction mixture comprising a) a toluene diamine having no substituents other than the required amino groups or having one or more substituents which are inert to the reaction conditions, b) a Lewis acid catalyst or organometallic catalyst, and c) an organic disulfide, said first reaction mixture forming a product mixture from which the desired thioalkylated toluene diamines are removed by thermal product recovery methods, the improvement comprising adding to said product mixture a chaser selected from the group consisting of alkylene diol, alkylene ether glycol, alkyl-terminated alkylene ether polymer and aryl-terminated alkylene ether polymer said chaser having the following properties: a) it is soluble in the organic compounds of the reaction mixture and b) it has a boiling point such that the chaser will not be removed from the product mixture prior to the recovery of the desired product and recycling the chaser and Lewis acid or organometallic catalyst by:
   i) separating the chaser and Lewis acid or organometallic catalyst from the product mixture, and
   ii) treating a second reaction mixture with the separated chaser and Lewis acid or organometallic catalyst.

4. The process of claims 1, 2 or 3 wherein the poly(oxyalkylene)polymer has a molecular weight of between about 150 and about 9,000.

5. The process of claims 1, 2 and 3 wherein the poly(oxyalkylene)polymer has a molecular weight of between about 400 and about 1,000.

6. The process of claims 1, 2 and 3 wherein the poly(oxyalkylene)polymer has a molecular weight of between about 500 and about 700.

7. The process of claims 1, 2 and 3 in which the organic disulfide contains from 1 to 6 carbons.

8. The process of claims 1, 2 and 3 in which the organic disulfide is dimethyldisulfide.

9. The process of claims 1, 2 and 3 in which the Lewis acid catalyst is aluminum chloride.

10. The process of claims 1, 2 and 3 in which the Lewis acid catalyst is zinc iodide.

11. The process of claims 1, 2 and 3 in which the Lewis acid catalyst is copper iodide.

12. The process of claims 2 and 3 in which the improvement comprising recycling the poly(oxyalkylene)polymer and Lewis acid or organometallic catalyst is repeated in a sequence of such processes for producing thioalkylated aromatic amines.

* * * * *